United States Patent [19]
Mantegani et al.

[11] Patent Number: 5,968,955
[45] Date of Patent: Oct. 19, 1999

[54] DISUBSTITUTED PIPERIDINE DERIVATIVES AS NEUROPROTECTIVE AGENTS

[75] Inventors: Sergio Mantegani, Milan; Tiziano Bandiera, Gambolò ; Manuela Villa, Lurago d'Erba; Mario Varasi, Milan; Carmela Speciale, Nerviano, all of Italy

[73] Assignee: Pharmacia & Upjohn S.p.A., Milan, Italy

[21] Appl. No.: 09/043,906

[22] PCT Filed: Sep. 16, 1996

[86] PCT No.: PCT/EP95/04075

§ 371 Date: Mar. 31, 1998

§ 102(e) Date: Mar. 31, 1998

[87] PCT Pub. No.: WO97/13769

PCT Pub. Date: Apr. 17, 1997

[30] Foreign Application Priority Data

Jun. 10, 1995 [GB] United Kingdom .................. 9520444

[51] Int. Cl.⁶ ...................... A61K 31/445; C07D 413/06
[52] U.S. Cl. ............................. 514/326; 546/209
[58] Field of Search ............... 546/209; 514/326

[56] References Cited

U.S. PATENT DOCUMENTS 4,397,853  8/1983  Kawakita et al. ................. 514/404
5,338,857  8/1994  Ohto et al. ........................ 548/248

OTHER PUBLICATIONS

Chemical Abstracts, vol. 78, No. 25, Jun. 25, 1973, Columbus Ohio, US; 159582y, p. 415; XP002020897 see abstract & JP 48 026 759 A (Shionogi and Co., Ltd) Apr. 9, 1973.
Chemical Abstracts, vol. 84, No. 15, Apr. 12, 1976, Columbus, Ohio, US; abstract No. 99377x, p. 42; XP002020898 see abstract & JPN.J.Pharmacol., pp. 501–505, Toshio Yoshizaki et al: "Drug–induced adrenaline release and blood glucose in rats:3–phenyl–5–(2–piperidinoethyl)isoxazo le citrate".

Chemical Abstracts, vol. 67, No. 11, Sep. 11, 1967, Columbus, Ohio, US; abstract No. 54119x, p. 5092; XP002020899 see abstract & JP 42 003 496 B (Shionogi and Col, Ltd) May 6, 1967.

*Primary Examiner*—Ceila Chang
*Attorney, Agent, or Firm*—Oblon, Spivak, McClelland, Maier & Neustadt, P.C.

[57] ABSTRACT

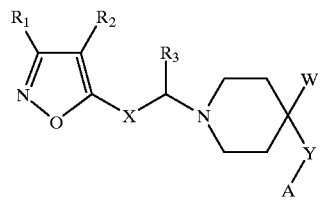

A Disubstituted piperidine compounds of formula (I), wherein $R_1$ is hydrogen; bromo; chloro; a linear or branched $C_1$–$C_5$ alkyl group; a linear or branched $C_1$–$C_5$ alkoxy group; or an optionally substituted phenyl group; $R_2$ is hydrogen, a linear or branched $C_1$–$C_5$ alkyl group or an optionally substituted phenyl group; X is $CH_2$, C=O, CHOH or C=NOH; $R_3$ is hydrogen or a linear or branched $C_1$–$C_5$ alkyl group; Y is a $(CH_2)_n$ group in which n is an integer from 0 to 4, CHOH, C=O or CH-A wherein A is an optionally substituted phenyl group; A is an optionally substituted phenyl group; W is hydrogen or hydroxy; stereoisomers thereof and their pharmaceutically acceptable salts. The compounds possess selective neuroprotective activity and are useful in the treatment of an acute or a degenerative CNS disease. A process is described for preparing the compounds and pharmaceutical compositions containing them.

9 Claims, No Drawings

DISUBSTITUTED PIPERIDINE DERIVATIVES AS NEUROPROTECTIVE AGENTS

This application is a 371 of PCT/EP96/04075 filed Sep. 16, 1996.

The present invention relates to disubstituted piperidine derivatives, to a process for their preparation and to pharmaceutical compositions containing them.

These compounds possess selective neuroprotective activity and can therefore be useful in the prevention and/or treatment of neurotoxic injuries associated with neurological insults or neurodegenerative diseases.

The exicitatory amino acids (EAAs) L-glutamate and L-aspartate are the most abundant amino acids in brain and play a number of roles in maintaining neuronal function. For example, EAA neurotransmitters may contribute to the cellular abnormalities associated with epilepsy, the brain damage characteristic of neurodegenerative disorders such as, e.g., Huntington's, Alzheimer's and Parkinson's diseases, as well as disorders associated with ischemia, head injury and AIDS encephalopathy. Moreover, these trasmitters play a crucial role in learning and memory (Life Science, Vol. 54, pp. 135–148, 1993).

Control of the above identified neurophatological processes and neurodegenerative consequences can be provided by compounds having activity as mediators or inhibitors of EAAs at the neuronal receptor sites.

There is therefore a need to find pharmacological agents able to antagonize or block neurotoxic action of EAAs at the EAA synaptic receptors of central neurons, in order to prevent and/or treat neurotoxic injuries associated with neurological insults or neurodegenerative diseases.

The compounds of the present invention fulfill such a need.

Accordingly, the present invention provides a 1,4-disubstituted piperidine derivative of formula (I)

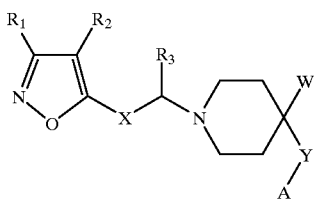

(I)

wherein

R$_1$ is hydrogen; bromo; chloro; a linear or branched C$_1$–C$_5$ alkyl group; a linear or branched C$_1$–C$_5$ alkoxy group; or an optionally substituted phenyl group of formula

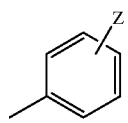

wherein Z is hydrogen, a linear or branched C$_1$–C$_5$ alkyl group, a linear or branched C$_1$–C$_5$ alkoxy group, bromo, chloro, fluoro, nitro or trifluoromethyl;

R$_2$ is hydrogen, a linear or branched C$_1$–C$_5$ alkyl group or an optionally substituted phenyl group as defined above;

X is CH$_2$, C=O, CHOH or C=NOH;

R$_3$ is hydrogen or a linear or branched C$_1$–C$_5$ alkyl group;

Y is a (CH$_2$)$_n$ group in which n is an integer from 0 to 4, CHOH, C=O or CH-A wherein A is an optionally substituted phenyl group as defined above;

A is an optionally substituted phenyl group as defined above;

W is hydrogen or hydroxy;

and the pharmaceutically acceptable salts thereof.

Depending on the different meanings of the substituents X, R$_3$ and/or Y, the compounds of formula (I) can have one or more asymmetric centers and can therefore exist in different stereoisomers which are also within the scope of the present invention.

A linear or branched C$_1$–C$_5$ alkyl group may be, for example, methyl, ethyl, n-propyl, isopropyl, n-butyl, sec-butyl, tert-butyl or n-pentyl; preferably, it is methyl, ethyl, propyl or iso-propyl.

A linear or branched C$_1$–C$_5$ alkoxy group may be, for a example, methoxy, ethoxy, n-propoxy, isopropoxy, n-butoxy or n-pentoxy; preferably, it is a linear C$_1$–C$_5$ alkoxy group, in particular a linear C$_1$–C$_3$ alkoxy group, more particularly methoxy or ethoxy.

Preferred meanings of the Z substituent in an optionally substituted phenyl group of formula

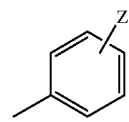

are hydrogen; chloro; bromo; fluoro; a linear C$_1$–C$_3$ alkoxy group, in particular methoxy; and trifluoromethyl. Most preferred meanings of Z are fluoro and methoxy. Substituent Z may be in ortho, meta or para position of the phenyl ring; preferably, it is in para position.

As mentioned above, the present invention includes also in its scope 1,4-disubstituted piperidine derivatives of formula (I) in the form of pharmaceutically acceptable salts; these salts may be with pharmaceutically acceptable acids, both inorganic and organic acids.

In this case, pharmaceutically acceptable salts refer to acid addition salts.

A pharmaceutically acceptable inorganic acid may be, e.g., hydrochloric, hydrobromic, sulfuric, nitric or phosphoric acid; a pharmaceutically acceptable organic acid may be, e.g., malic, maleic, pamoic, succinic, gluconic, citric, tartaric, ascorbic, acetic, methanesulphonic or benzensulphonic acid.

A preferred class of compounds according to this invention are compounds of formula (I) wherein R$_1$ is hydrogen; bromo; chloro; a linear C$_1$–C$_3$ alkoxy group or an optionally substituted phenyl group of formula

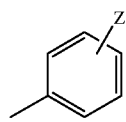

wherein Z is hydrogen, bromo, fluoro, a linear C$_1$–C$_3$ alkoxy group or trifluoromethyl; R$_2$ is hydrogen, a linear or branched C$_1$–C$_5$ alkyl group or an optionally substituted phenyl group as defined above;

X is CH$_2$, CHOH, C=O or C=NOH;

R$_3$ is hydrogen or a linear or branched C$_1$–C$_5$ alkyl group;

Y is a (CH$_2$)$_n$ group in which n is zero or 1, C=O or CH-A wherein A is an optionally substituted phenyl group as defined above;

A is an optionally substituted phenyl group as defined above;

W is hydrogen or hydroxy; and their pharmaceutically acceptable salts.

Examples of specific compounds of the invention are:
1) 2-(4-benzyl-piperidin-1-yl)-1-(3-bromo-isoxazol-5-yl)-ethan-1-ol;
2) 2-(4-benzyl-piperidin-1-yl)-1-(3-bromo-isoxazol-5-yl)-propan-1-ol;
3) 2-(4-benzyl-piperidin-1-yl)-1-(3-methoxy-isoxazol-5-yl)-ethan-1-ol;
4) 2-(4-benzyl-piperidin-1-yl)-1-(3-methoxy-isoxazol-5-yl)-propan-1-ol;
5) 2-(4-benzyl-4-hydroxy-piperidin-1-yl)-1-(3-bromo-isoxazol-5-yl)-ethan-1-ol;
6) 2-(4-benzyl-4-hydroxy-piperidin-1-yl)-1-(3-bromo-isoxazol-5-yl)-propan-1-ol;
7) 2-(4-benzyl-4-hydroxy-piperidin-1-yl)-1-(3-methoxy-isoxazol-5-yl)-ethan-1-ol;
8) 2-(4-benzyl-4-hydroxy-piperidin-1-yl)-1-(3-methoxy-isoxazol-5-yl)-propan-1-ol;
9) (4-benzyl-piperidin-1-yl)-1-(3-bromo-isoxazol-5-yl)-ethane;
10) 2-(4-benzyl-piperidin-1-yl)-1-(3-methoxy-isoxazol-5-yl)-ethane;
11) 2-(4-benzyl-piperidin-1-yl)-1-(3-bromo-isoxazol-5-yl)-propane;
12) 2-(4-benzyl-piperidin-1-yl)-1-(3-methoxy-isoxazol-5-yl)-propane;
13) 2-(4-benzyl-piperidin-1-yl)-1-(3-bromo-isoxazol-5-yl)-ethanone;
14) 2-(4-benzyl-piperidin-1-yl)-1-(3-bromo-isoxazol-5-yl)-propan-1-one;
15) 2-(4-benzyl-piperidin-1-yl)-1-(3-methoxy-isoxazol-5-yl)-ethanone;
16) 2-(4-benzyl-piperidin-1-yl)-1-(3-methoxy-isoxazol-5-yl)-propan-1-one;
17) 2-(4-benzyl-piperidin-1-yl)-1-(3-bromo-isoxazol-5-yl)-ethan-1-one-oxyme;
18) 2-(4-benzyl-piperidin-1-yl)-1-(3-bromo-isoxazol-5-yl)-propan-1-one-oxyme;
19) 2-(4-benzyl-piperidin-1-yl)-1-(3-methoxy-isoxazol-5-yl)-ethan-1-one-oxyme;
20) 2-(4-benzyl-piperidin-1-yl)-1-(3-methoxy-isoxazol-5-yl)-propan-1-one-oxyme;
21) 2-(4-benzoyl-piperidin-1-yl)-1-(3-bromo-isoxazol-5-yl)-ethan-1-ol;
22) 2-(4-benzoyl-piperidin-1-yl)-1-(3-bromo-isoxazol-5-yl)-propan-1-ol;
23) 2-(4-benzoyl-piperidin-1-yl)-1-(3-methoxy-isoxazol-5-yl)-ethan-1-ol;
24) 2-(4-benzoyl-piperidin-1-yl)-1-(3-methoxy-isoxazol-5-yl)-propan-1-ol;
25) 2-[4-(4-fluoro-benzoyl)piperidin-1-yl]-1-(3-bromo-isoxazol-5-yl)-ethan-1-ol;
26) 2-[4-(4-fluoro-benzoyl)piperidin-1-yl]-1-(3-bromo-isoxazol-5-yl)-propan-1-ol;
27) 2-[4-(4-fluoro-benzoyl)piperidin-1-yl]-1-(3-methoxy-isoxazol-5-yl)ethan-1-ol;
28) 2-[4-(4-fluoro-benzoyl)piperidin-1-yl]-1-(3-methoxy-isoxazol-5-yl)propan-1-ol;
29) 2-(4-diphenylmethyl-piperidin-1-yl)-1-(3-bromo-isoxazol-5-yl)-propan-1-ol;
30) 2-(4-diphenylmethyl-piperidin-1-yl)-1-(3-bromo-isoxazol-5-yl)-ethan-1-ol;
31) 2-(4-diphenylmethyl-piperidin-1-yl)-1-(3-methoxy-isoxazol-5-yl)-propan-1-ol;
32) 2-(4-diphenylmethyl-piperidin-1-yl)-1-(3-methoxy-isoxazol-5-yl)-ethan-1-ol;
33) 2-(4-phenyl-4-hydroxy-piperidin-1-yl)-1-(3-bromo-isoxazol-5-yl)-ethan-1-ol;
34) 2-(4-phenyl-4-hydroxy-piperidin-1-yl)-1-(3-bromo-isoxazol-5-yl)-propan-1-ol;
35) 2-(4-phenyl-4-hydroxy-piperidin-1-yl)-1-(3-methoxy-isoxazol-5-yl)-ethan-1-ol;
36) 1-(4-phenyl-4-hydroxy-piperidin-1-yl)-1-(3-methoxy-isoxazol-5-yl)-propan-1-ol;
37) 2-(4-phenyl-4-hydroxy-piperidin-1-yl)-1-(3-bromo-isoxazol-5-yl)-ethane;
38) 2-(4-phenyl-4-hydroxy-piperidin-1-yl)-1-(3-bromo-isoxazol-5-yl)-propane;

if the case, either as single isomer or as racemic mixture, and their pharmaceutically acceptable salts.

The compounds of formula (I) may be prepared by a process comprising:

(a) reacting a compound of formula (II)

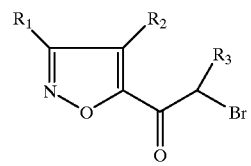

(II)

wherein $R_1$ is hydrogen, bromo; chloro; a linear or branched $C_1$–$C_5$ alkyl group; a linear branched $C_1$–$C_5$ alkoxy group; or an optionally substituted phenyl group of formula

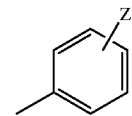

wherein Z is hydrogen, a linear or branched $C_1$–$C_5$ alkyl group, a linear or branched $C_1$–$C_5$ alkoxy group, bromo, chloro, fluoro, nitro or trifluoromethyl;

$R_2$ is hydrogen, a linear or branched $C_1$–$C_5$ alkyl group or an optionally substituted phenyl group as defined above; and $R_3$ is hydrogen or a linear or branched $C_1$–$C_5$ alkyl group;

with a compound of formula (III)

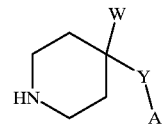

(III)

wherein

Y is a (CH$_2$)$_n$ group in which n is an integer of 0 to 4, CHOH, C=O, or CH-A wherein A is an optionally substituted phenyl group as defined above;

A is an optionally substituted phenyl group as defined above; and

W is hydrogen or hydroxy;
to obtain a compound of formula (I) wherein $R_1$, $R_2$, $R_3$, Y, A and W are as defined above and X is a C=O group; and, if desired, converting a compound of formula (I) as obtained above, into another compound of formula (I) wherein X is CHOH or $CH_2$; or (b) reacting a compound of formula (IV)

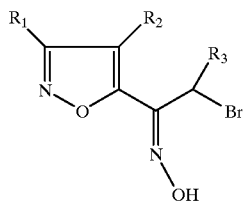

(IV)

wherein $R_1$, $R_2$, and $R_3$ have the meanings above mentioned, with a compound of formula (III) as defined above, to obtain a compound of formula (I) wherein $R_1$, $R_2$, $R_3$, Y, A and W are as defined above and X is a C=NOH group; or (c) reacting a compound of formula (V)

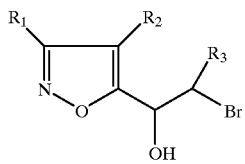

(V)

wherein $R_1$, $R_2$ and $R_3$ have the meanings above mentioned, with a compound of formula (III) as defined above, to obtain a compound of formula (I) wherein $R_1$, $R_2$, $R_3$, Y, A and W are as defined above and X is a CHOH group; or (d) reacting a compound of formula (VI)

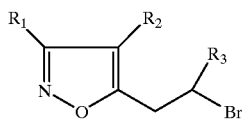

(VI)

wherein $R_1$, $R_2$ and $R_3$ have the meanings above mentioned, with a compound of formula (III) as defined above, to obtain a compound of formula (I) wherein $R_1$, $R_2$, $R_3$, Y, A and W are as defined above and X is $CH_2$; and, if desired, (e) converting a compound of formula (I) into a pharmaceutically acceptable salt thereof.

The reaction described as step (a) may be carried out, for example, by reacting a compound of formula (II) with a piperidine derivative of formula (III) in a solvent such as, e.g., tetrahydrofurane (THF) or ethanol, in the presence of a proton scavenger such as, e.g.,triethylamine (TEA) or Hônig's base, at a temperature ranging, e.g., from about 0° C. to about 35° C. The optional conversion which allows to obtain a compound of formula (I) wherein X is CHOH, from a compound of formula (I) wherein X is C=O may be carried out, for example, by reacting a compound of formula (I) wherein X is C=O with a suitable reducing agent such as, e.g., $NaBH_4$ in a suitable solvent such as, e.g., ethanol or isopropanol at a temperature, for example, of about 0° C. The optional conversion which allows to obtain a compound of formula (I) wherein X is $CH_2$ from a compound of formula (I) wherein X is C=O may be carried out, for example, by reacting a compound of formula (I) wherein X is C=O with a suitable reducing agent such as, e.g. $(C_2H_5)_3SiH$ in a suitable solvent such as, e.g. trifluoro acetic acid at a temperature ranging, e.g., from about −100° C. to about 35° C.

The reaction described as step (b) may be carried out, for example, by reacting a compound of formula (IV) with a piperidine derivative of formula (III) in a solvent such as, e.g., THF or ethanol, in the presence of a proton scavenger such as, e.g., TEA, Hônig's base or $K_2CO_3$, at a temperature ranging, e.g., from about 0° C. to about 100° C.

The reaction described as step (c) may be carried out, for example, by reacting of a compound of formula (V) with a piperidine derivative of formula (III) in a solvent such as, e.g., dimethylformamide (DMF) or dimethoxyethane (DME) in the presence of a proton scavenger such as, e.g.,TEA, Hônig's base or $K_2CO_3$ at a temperature ranging, e.g., from about 0° C. to about 120° C.

The reaction described as step (d) may be carried out, for example, by reacting a compound of formula (IV) with a piperidine derivative of formula (III) in a solvent such as, e.g., DME or ethanol in the presence of a proton scavenger such as, e.g., TEA or Hônig's base at a temperature ranging, e.g., from about 20° C. to about 75° C.

The optional conversion of a compound of formula (I) into a salt thereof described as step (e) may be carried out, for example, by adding a stoichiometric amount of a suitable pharmaceutically acceptable acid dissolved in a suitable solvent such as, e.g., diethylether, ethanol or methanol to a solution of the base. The salt can be recovered by concentration of the solution.

The starting compounds of formula (II), (III), (IV), (V) and (VI) are commercially available compounds or can be obtained from commercially available compounds following known procedures.

As already said, depending on the meaning of the substituents X, $R_3$, and/or Y, the compounds of formula (I) can have one or more asymmetric centers and can therefore exist in different stereoisomers which are also within the scope of the present invention. The stereoisomers can be obtained by separation from as their mixture or, alternatively, they can be prepared by stereoselective synthesis following known methods widely reported in the literature.

For example, the racemate can be resolved into the single enantiomers by crystallization of the diastereomeric acid addition salts obtained via an optically active acid such as, e.g., tartaric, dibenzoyltartaric, camphoric, or camphorsulphonic acid, or, when in a compound of formula (I) X is CHOH, the racemic mixture can be resolved by conversion into the corresponding diastereomeric ester or carbamate by using an appropriate optically active activated acid derivative or isocyanate.

After separation of the diastereoisomers by crystallization or chromatography, the pure enantiomers can be recovered by saponification or by alcoholysis.

In alternative, as said above, the optically active compounds of formula (I) can be prepared in stereoselective manner either starting from optically pure material or using optically active reagents.

All the racemic mixture and the pure optical isomers of the compounds of the present invention are within the scope of the invention.

The compounds of general formula (I) and their pharmaceutically acceptable salts possess selective neuroprotective activity, based upon their antiischemic activity and ability to block excitatory amino acid receptors.

In view of such activities, the compounds of the present invention are useful in the treatment of acute or degenerative CNS pathologies such as, e.g., epilepsy, Parkinson's disease, Huntington's disease and Alzheimer's disease.

The neuroprotective and antiischemic activities of the compounds of the present invention were assessed in vivo and in vitro following the methods described below.

The antiischemic activity of the compounds of the present invention was evaluated in vivo in the model of focal ischemia in mice.

Focal ischemia was produced in mice by electrocoagulation of the Middle Cerebral Artery (MCA) according the procedure reported by Welsh et al. (Welsh F A, Sakamoto T, McKee A, Sims R E, J Neurochem: 49: 846–851, 1987). Briefly, male Swiss CD mice (C. River, Milan, Italy) were anesthetised with chloral hydrate (500 mg/Kg i.p.); an incision was made on the temporo-parietal region of the head and a small burr hole was drilled into the lateral outer surface of the skull just over the MCA. The stem of the MCA was occluded by microbipolar coagulation. Animals were maintained under an heating lamp during surgery and for two hours afterwards.

Four days after the occlusion, mice were decapitated and the brains stored a $-20°$ C. until sectioned for histological examination.

Coronal sections (50 $\mu$m thick) of the frozen brains were taken every 1.00 mm in order to evaluate the infarct volume.

The slices were stained with cresyl violet and the cortical infarct area of each slice was determined by an image analyzing system (Ibas 20, Kontron, Milan, Italy). Infarct volume was calculated from the infarct area on each slice and the distance between succeeding slices.

The treatment schedule consisted in the administration of the tested compound 5 min and 6 h after ischemia during the first day after surgery and then twice a day on days 2, 3 and 4 according to published data (Gotti B. et al.; Brain Research, 522,290–307, 1990). The tested compounds were given i.p. at the dose of 7 mg/Kg.

Dosing was performed till sacrifice. The time schedule, the doses and the route of administration of the tested compounds were selected on the basis of preliminary experiments.

For instance, a compound of the invention, (±)-2-(4-benzyl-piperidin-1-yl)-1-(3-methoxy-isoxazol-5-yl)-ethan-1-ol, was tested according to the method described above, in order to evaluate its antiischemic activity in vivo.

The obtained results are reported in Table 1 below.

TABLE 1

| Compound | n | Infarct volume (mm$^3$) |
|---|---|---|
| Saline | 23 | 20.9 ± 1.7 |
| (±)-2-(4-benzyl-piperidin-1-yl)-1-(3-methoxy-isoxazol-5-yl)-ethan-1-ol | 24 | 13.6 ± 1.5 |

P < 0.01 from controls
(1) Infarct volume (Means ± SEM) after MCA occlusion in male Swiss mice treated according to protocols described in the methods.

Infarct volume on day 4 was 20.9±1.7 mm$^3$ (n=23) in mice treated with saline solution.

The compound of Example 2 was found to significantly reduce infarct volume (13.6±1.5) when compared with infarct volume registered in mice treated with saline solution (20.9±1.7 mm$^3$).

The compounds of formula (I) and their pharmaceutically acceptable salts possess selective neuroprotective activity. The efficacy of the compounds of the invention as neuroprotective agents, based upon their ability to prevent EEA induced toxicity in vitro, was evaluated in mixed cortical neuronal cultures, following the method reported below.

Mixed cortical neuronal cultures from foetal rats at 16 days of gestation were prepared as described by Choi (J. Neur. Sci. 7: 357–368, 1987).

Briefly, dissociated cells were plated on poly-L-lysine coated multiwell plates at density of $1*10^5$ cells/cm$^2$ in MEM with Earle's salts supplemented with 21 mM D-glucose, 2 mM L-glutamine, 50 $\mu$g/ml Streptomicin, 50 IU Penicillin, 10% Foetal Calf Serum and 10% Horse Serum. Cultures were kept at 37° C., 5% $CO_2$ and survived about 5 weeks. After 7 days in vitro, astrocites proliferation was inhibited by adding 10 $\mu$M Cytosine Arabinoside for 48 hours; the medium was subsequently substituted twice a week with a fresh medium without foetal calf serum (Hatley, J. Pharm. and Exp. Ther. 250 (II);752–758, 1989).

Only nature cortical cultures, from 14 DIV on, were used for the study.

Experiments were performed at 25° C. as follows: cells were washed once with a Locke's buffer, (128 mM NaCl, 25 nM KCl, 1.2 mM $Na_2HPO_4$, 2.7 mM $CaCl_2$, 20 mM Hepes and 10 mM D-glucose) pH=7.4, then preincubated with the test compounds for 3 min. followed by a 20 min. exposure to N-methyl-D-aspartate (NMDA) (500 $\mu$M).

The incubation was stopped by removing Locke's buffer and substituting the conditioned medium. After 24 hours at 37° C., 5% $CO_2$, Trypan Blue Dye Exclusion Test (0.04%) was used for evaluating the cells viability.

As an example, the neuroprotective effects of a representative group of compounds of the present invention, namely:
3) 2-(4-benzyl-piperidin-1-yl)-1-(3-methoxy-isoxazol-5-yl)-ethan-1-ol;
1) 2-(4-benzyl-piperidin-1-yl)-1-(3-bromo-isoxazol-5-yl)-ethan-1-ol;
25) 2-[4-(4-fluorobenzoyl)-piperidin-1-yl]-1-(3-bromo-isoxazol-5-yl)-ethan-1-ol;
27) 2-[4-(4-fluorobenzoyl)-piperidin-1-yl]-1-(3-methoxy-isoxazol-5-yl)-ethan-1-ol; and
17) 2-(4-benzyl-piperidin-1-yl)-1-(3-bromo-isoxazol-5-yl)-ethan-1-one-oxyme;

were tested in the cultured cortical neurons, following the method reported above.

The obtained results are reported in Table 2 below.

TABLE 2

| Compound | $EC_{50}$ $\mu$M |
|---|---|
| 2-(4-benzyl-piperidin-1-yl)-1-(3-methoxy-isoxazol-5-yl)-ethan-1-ol | 3.29 |
| 2-(4-benzyl-piperidin-1-yl)-1-(3-bromo-isoxazol-5-yl)-ethan-1-ol | 2.02 |
| 2-[4-(4-fluorobenzoyl)-piperidin-1-yl]-1-(3-bromo-isoxazol-5-yl)-ethan-1-ol | 22 |
| 2-[4-(4-fluorobenzoyl)-piperidin-1-yl]-1-(3-methoxy-isoxazol-5-yl)-ethan-1-ol | 0.64 |
| 2-(4-Benzyl-piperidin-1-yl)-1-(3-bromo-isoxazol-5-yl)-ethan-1-one-oxyme | 2.13 |

A human or animal body may thus be treated by a method which comprises the administration thereto of a pharmaceutically effective amount of a compound of formula (I) or salt thereof.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion; topically, e.g. in the form of creams. Preferably they are administered by oral or parenteral route, more preferably by oral route.

The dosage depends on the age, weight, conditions of the patient and administration route. For example, the compounds of the present invention can be administered, e.g., in a daily dose, generally in a range from about 0.1 mg to about 25 mg per kilogram of body weight per day. A suitable dose can be administered, for example, in sub-doses per day.

The present invention also provides pharmaceutical compositions comprising a compound of formula (I) or a pharmaceutically acceptable salt thereof, in association with a pharmaceutically acceptable excipient, which can be a carrier or a diluent.

The pharmaceutical compositions containing the compounds of the invention are usually prepared following conventional methods and are administered in a pharmaceutically suitable form.

For example, the solid oral form may contain, together with the active compound, diluents, e.g. lactose, dextrose, cellulose, corn starch or potato starch; lubricants, e.g. silica, talc, stearic acid, magnesium or calcium stearate, and/or polyethylene glycols; binding agents, e.g. starches, arabic gums, gelatins, methylcellulose or polyvinyl pirrolidone; and, in general, non toxic and inactive substances used in pharmaceutical formulations.

These pharmaceutical preparations may be manufactured in a known manner, for example, by means of mixing, granulating, tabletting, sugar-coated, or film-coating processes.

The liquid dispersion for oral administration, may be e.g. syrup, emulsions or suspensions. The syrups may contain as carrier, for example, saccharose or saccharose with glycerine and/or mannitol and/or sorbitol.

The suspensions and the emulsions may contain as carrier, for example, a natural gum, agar, sodium alginate, pectine or polyvinyl alcohol.

The suppositories may contain together with the active compound a pharmaceutically acceptable carrier, e.g. cocoa-butter, polyethylen glycol, or lecithin.

The following examples illustrate but do not limit the present invention.

EXAMPLE 1

1) (±)-2-(4-Benzyl-piperidin-1-yl)-1-(3-bromo-isoxazol-5-yl) -ethan-1-ol

A solution of 6.0 g of 1-(3-bromoisoxazol-5-yl)-2-bromoethanol and 11.7 ml of 4-benzylpiperidine in 150 ml of ethanol was refluxed for 2 hours.

The solvent was removed in vacuo and the residue was taken up in ethyl acetate and the resulting precipitate of 4-benzylpiperidine hydrochloride was filtered off. The reaction mixture was chromatographed on silica gel eluting with ethylacetate/cyclohexane 1/1.

The fraction containing the product were pooled and after removal of the solvent, the residue was crystallized from di-isopropyl ether, affording 1 g of the title compound as white crystals in 12% yield, m.p. 125–127° C.

$^1$H-NMR (DMSO-d$^6$): δ 7.2 (m, 5 H, Ph), δ 6.66 (s, 1 H, CH isox.), δ 5.69 (d broad, 1 CHOH.), δ 2.8 (t broad, 2 H eq.), δ 2.45 (d, 2 H, CH2N), δ 2.41 (d, 2 H, CH2Ph)δ 1.19 (m, 2 H ax.), δ 1.45 (m, 2 H eq+1H4'.), δ 1.15 (m, 2 H ax.).

EXAMPLE 2

3) (±)-2-(4-Benzyl-piperidin-1-yl)-1-(3-methoxy-isoxazol-5-yl)-ethan-1-ol

Operating as in Example 1, but employing 1-(3-methoxy-isoxazol-5-yl)-2-bromoethanol instead of 1-(3-bromo-isoxazol-5-yl)-2-bromoethanol, the title compound was obtained in 23% yield, m.p. 134–137° C.

$^1$H-NMR (DMSO-d$^6$): δ 7.2 (m, 5 H, Ph), δ 6.66 (s, 1 H, CH isox.), δ 5.69 (d broad, 1 H, CHOH.), δ 3.85 (s, 3 H, CH$_3$O), δ 2.7 (t broad, 2 H eq.), δ 2.46 (d, 2 H, CH2N), δ 2.41 (d, 2 H, CH2Ph), δ 1.17 (m, 2 H ax.), δ 1.45 (m, 2 H eq+1H4'.), δ 1.15 (m, 2 H ax.).

EXAMPLE 3

35) 2-(4-phenyl-4-hydroxy-piperidin-1-yl)-1-(3-methoxy-isoxazol-5-yl) -ethan-1-ol Operating as in Example 1, but employing 4-hydroxy-4-phenyl-piperidine instead of 4-benzyl-piperidine, the title compound was obtained in 22% yield, m.p. 166–168° C.

$^1$H-NMR (DMSO-d$^6$): δ 8.55–7.1 (m, 5 H, arom.), δ 6.12 (s, 1 H), δ 5.61 (d, 1 H, CHOH), δ 4.68 (s, 1 H, —COH (C$_6$H$_5$)—), δ 4.61 (m, 1 H, CHOH) δ 3.84 (s, 3 H, OCH3) δ 2.8–2.94 (m 8 H) δ 2–1.8 (m, 1 H), δ 1.62–1.5 (m, 1 H).

EXAMPLE 4

9) 2-(4-benzyl-piperidin-1-yl)-1-(3-bromo-isoxazol-5-yl)-ethane hydrochloride

Operating as in Example 1, but employing of 1-(3-bromo-isoxazol-5-yl) -2-bromoethane, instead of 1-(3-bromo-isoxazol-5-yl)-2-bromoethanol, the title compound was obtained in 27% yield, m.p. 190–194° C.

$^1$H-NMR (DMSO-d$^6$): δ 9.7 (m broad, 1H, N-H+), δ 7.21 (m, 5H, Ph), δ 6.78 (s, 1 H, H-isox.), δ 3.6–2.4 (m, 8H), δ 1.82–1.2 (m, 7 H)

EXAMPLE 5

10) 2-(4-benzyl-piperidin-1-yl)-1-(3-methoxy-isoxazol-5-yl)-ethane hydrochloride Operating as in Example 1, but employing of 1-(3-methoxy-isoxazol-5-yl)-2-bromoethane, instead of 1-(3-methoxy-isoxazol-5-yl)-2-bromoethanol,the title compound was obtained in 24% yield, m.p. 175–179° C.

$^1$H-NMR (DMSO-d$^6$): δ 7.2 (m, 5H, Ph), δ 5.98 (s, 1 H-isox.), δ 3.81 (s, 3 H, CH$_3$O.), δ 2.85–2.4 (m, 8H), δ1.91 (m, 7 H, pip.)

EXAMPLE 6

32) 2-(4-diphenylmethyl-piperidin-1-yl)-1-(3-methoxy-isoxazol-5-yl)-ethan-1-ol

Operating as in Example 2, but employing 4-diphenylmethyl-piperidine instead of 4-benzyl-piperidine, the title compound was obtained in 12% yield, m.p. 121–126° C.

$^1$H-NMR (DMSO-d$^6$): δ 7.24 (m, 10 H, 2 Ph), δ 6.06 (s, 1 H, CH isox.), δ 5.58 (d, 1 H, CHOH), δ 4.64 (m, 1 H, —CHOH), δ 3.84 (s, 3 H, OCH3), δ (d, 1 H, CH(Ph)$_2$) δ 2.8 (m, 2 H), δ (d, 2 H, CH$_2$N), δ 2.16 (m, 1 H), δ 2 (m, 2 H), δ 1.34 (m 2 H), ), δ 1.1 (m, 2 H)

Following analogous procedure, the below listed compounds can be prepared:
5) 2-(4-benzyl-4-hydroxy-piperidin-1-yl)-1-(3-bromo-isoxazol-5-yl)-ethan-1-ol;
6) 2-(4-benzyl-4-hydroxy-piperidin-1-yl)-1-(3-bromo-isoxazol-5-yl)-propan-1-ol;
7) 2-(4-benzyl-4-hydroxy-piperidin-1-yl)-1-(3-methoxy-isoxazol-5-yl)-ethan-1-ol;
8) 2-(4-benzyl-4-hydroxy-piperidin-1-yl)-1-(3-methoxy-isoxazol-5-yl)-propanol-1-ol;

2) 2-(4-benzyl-piperidin-1-yl)-1-(3-bromo-isoxazol-5-yl)-propan-1-ol;
4) 2-(4-benzyl-piperidin-1-yl)-1-(3-methoxy-isoxazol-5-yl)-propan-1-ol;
11) 2-(4-benzyl-piperidin-1-yl)-(3-bromo-isoxazol-5-yl)-propane;
12) 2-(4-benzyl-piperidin-1-yl)-1-(3-methoxy-isoxazol-5-yl)-propane;
13) 2-(4-benzyl-piperidin-1-yl)-1-(3-bromo-isoxazol-5-yl)-ethanone;
14) 2-(4-benzyl-piperidin-1-yl)-1-(3-bromo-isoxazol-5-yl)-propan-1-one;
15) 2-(4-benzyl-piperidin-1-yl)-1-(3-methoxy-isoxazol-5-yl)-ethanone;
16) 2-(4-benzyl-piperidin-1-yl)-1-(3-methoxy-isoxazol-5-yl)-propan-1-one;
33) 2-(4-phenyl-4-hydroxy-piperidin-1-yl)-1-(3-bromo-isoxazol-5-yl)-ethan-1-ol;
34) 2-(4-phenyl-4-hydroxy-piperidin-1-yl)-1-(3-bromo-isoxazol-5-yl)-propan-1-ol;
36) 2-(4-phenyl-4-hydroxy-piperidin-1-yl)-1-(3-methoxy-isoxazol-5-yl)-propan-1-ol;
37) 2-(4-phenyl-4-hydroxy-piperidin-1-yl)-1-(3-bromo-isoxazol-5-yl)-ethane;
38) 2-(4-phenyl-4-hydroxy-piperidin-1-yl)-1-(3-bromo-isoxazol-5-yl)-propane;
29) 2-(4-diphenylmethyl-piperidin-1-yl)-1-(3-bromo-isoxazol-5-yl)-propan-1-ol;
30) 2-(4-diphenylmethyl-piperidin-1-yl)-1-(3-bromo-isoxazol-5-yl)-ethan-1-ol; and
31) 2-(4-diphenylmethyl-piperidin-1-yl)-1-(3-methoxy-isoxazol-5-yl)-propan-1-ol.

EXAMPLE 7

27) (±)2-[4-(p-Fluoro-benzoyl)-piperidin-1-yl]-1-(3-methoxy-isoxazol-5-yl)-ethan-1-ol A solution of 3.5 g of 1-(3-methoxy-isoxazol-5-yl)-2-bromoethanol and 4.9 g of 4-(4'-fluorobenzoyl)piperidine and 5.4 ml of N-ethyldiisopropylamine in 160 ml of absolute ethanol was refluxed for 2 hours.

The solvent was removed in vacuo and ethyl acetate was added to remove N-ethyldiisopropylamine hydrochloride.

The reaction mixture was chromatographed on silica gel eluting with ethyl acetate/cyclohexane 3/7.

The fraction containing the compound were pooled, the solvent removed and after crystallization from di-isopropyl ether, 1.6 g of the title compound as brown crystals were obtained in 29% yield, m.p. 125–128° C.

$^1$H-NMR (DMSO-d$^6$): δ 8.05 (m, 2 H, arom.), δ 7.35 (m, 2 H, arom.), δ 6.08 (s, 1 H, CH isox.), δ 5.61 (d, 1 H, OH), δ 4.7 (q, 1 H, CHOH), δ 3.82 (s, 3 H, OCH3), δ 3.3 (m, 1 H4'), δ 2.9 (m, 2 H eq.2'/6'), δ 2.6 (d, 2 H, CH2N), δ 2.2 (m, 2 H ax., 2'/6'), δ 1.7 (m, 2 H eq., 3'/5'), δ 1.55 (m, 2 H ax., 3'/5').

EXAMPLE 8

25) 2-[4-(4-fluoro-benzoyl)piperidin-1-yl]-1-(3-bromo-isoxazol-5-yl)-ethan-1-ol

Operating as in example 7, but employing 1-(3-methoxy-isoxazol-5-yl)-2-broethanol instead of 1-(3-bromo-isoxazol-5-yl)-2-broethanol, the title compound was obtained in 17% yield, m.p. 132–135° C.

$^1$H-NMR (DMSO-d$^6$): δ 8.05 (m, 2 H, arom.), δ 7.37 (m, 2 H, arom.), δ 6.08 (s, 1 H, CH isox.), δ 5.61 (d, 1 H, OH), δ 4.7 (q, 1 H, CHOH), δ 3.35 (m, 1 H4'), δ 2.9 (m, 2 H eq. 2'/6'), δ 2.6 (d, 2 H, CH2N), δ 2.2 (m, 2 H ax., 2'/6'), δ 1.7 (m, 2 H eq., 3'/5'), δ 1.55 (m, 2 H ax., 3'/5').

Following analogous procedure, the below listed compounds can be prepared:

21) 2-(4-benzoyl-piperidin-1-yl)-1-(3-bromo-isoxazol-5-yl)-ethan-1-ol;
22) 2-(4-benzoyl-piperidin-1-yl)-1-(3-bromo-isoxazol-5-yl)-propan-1-ol;
26) 2-[4-(4-fluoro-benzoyl)piperidin-1-yl]-1-(3-bromo-isoxazol-5-yl)-propan-1-ol;
23) 2-(4-benzoyl-piperidin-1-yl)-1-(3-methoxy-isoxazol-5-yl)-ethan-1-ol;
24) 2-(4-benzoyl-piperidin-1-yl)-1-(3-methoxy-isoxazol-5-yl)-propan-1-ol; and
28) 2-[4-(4-fluoro-benzoyl)piperidin-1-yl]-1-(3-methoxy-isoxazol-5-yl)-propan-1-ol.

EXAMPLE 9

17) (±)-2-(4-Benzyl-piperidin-1-yl)-1-(3-bromo-isoxazol-5-yl)-ethan-1-one-oxyme

A solution of 2.2 g of 3-methoxy-5-bromoacetyl-isoxazole and 1.4 g of hydroxylamine hydrochloride in 30 ml of absolute ethanol was refluxed for 2 hours.

The solvent was removed, then after addition of water the formed precipitate was collected, washed with water then dried affording 2.1 g of 1-(3-methoxy-isoxazol-5-yl)-1-oxyimino-2-bromo-ethane as a mixture of geometrical isomers.

$^1$H-NMR (DMSO-d$^6$): δ 12.95 (s, 1 H, N-OH), δ 12.85 (s, 1 H, N-OH), δ 6.92 (s, 1 H, H isox.), δ 6.68 (s, 1 H, H isox.), δ 4.63 (s, 2 H, CH2Br), δ 4.47 (s, 2 H, CH2Br), δ 3.93 (s, 3 H, OCH3), δ 3.90 (s, 3 H, OCH3).

A solution of 2.5 g of the above described oxyme and 12 ml of 4-benzylpiperidine in 60 ml of absolute ethanol was refluxed for 5 hours.

The precipitated formed during the reaction, was collected washed with little ethanol then crystallizes twice from di-isopropylether affording 2.2 g of the title compound in 72% yield, m.p. 165–167° C.

$^1$H-NMR (DMSO-d$^6$): δ 12.35 (s broad, 1 H, N-OH), δ 7.18 (m, 5 H, Ph), δ 6.78 (s, 1 H, CH isox.), δ 3.90 (s, 3 H, OCH3), δ 3.32 (s, 2 H, CH2N), δ 2.79 (d broad, 2 H eq., 2'/6' pip.), δ 2.4 (s, 2 H, CH2Ph), δ 1.88 (t broad, 2H ax., 2'/6'), 1.47 (d broad, 2 H eq.,3'/5'+1H4'), δ 1.1 (m, 2 H ax.,3'/5').

Following analogous procedure the below listed compounds can be prepared:

18) 2-(4-piperidin-1-yl)-1-(3-bromo-isoxazol-5-yl)-propan-1-one-oxyme;
19) 2-(4-benzyl-piperidin-1-yl)-1-(3-methoxy-isoxazol-5-yl)-ethanone-oxyme; and
20) 2-(4-benzyl-piperidin-1-yl)-1-(3-methoxy-isoxazol-5-yl)-propan-1-one-oxyme.

EXAMPLE 10

Tablets each dosed at 110 mg containing 15 mg of the active substance can be prepared as follows.

| | |
|---|---|
| (±)-2-(4-Benzyl-piperidin-1-yl)-1-(3-methoxy-isoxazol-5-yl)-ethan-1-ol | 15 mg |
| Lactose | 80 mg |
| Starch (maize) | 10 mg |
| Magnesium Stearate | 5 mg |

This formulation can be prepared by direct compression of the admixed ingredients.

We claim:
1. A disubstituted piperidine compound of formula (I)

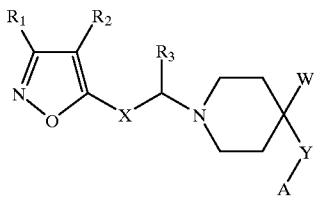

(I)

wherein
R$_1$ is hydrogen; bromo; chloro; a linear or branched C$_1$–C$_5$ alkyl group; a linear or branched C$_1$–C$_5$ alkoxy group;
or an optionally substituted phenyl group of formula

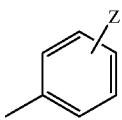

wherein Z is hydrogen, a linear or branched C$_1$–C$_5$ alkyl group, a linear or branched C$_1$–C$_5$ alkoxy group, bromo, chloro, fluoro, nitro or trifluoromethyl;
R$_2$ is hydrogen, a linear or branched C$_1$–C$_5$ alkyl group or an optionally substituted phenyl group as defined above;
X is CH$_2$, CHOH or C=NOH;
R$_3$ is hydrogen or a linear or branched C$_1$–C$_5$ alkyl group;
Y is a (CH$_2$)$_n$ group in which n is an integer from 0 to 4, CHOH, C=O or CH-A wherein A is an optionally substituted phenyl group as defined above;
A is an optionally substituted phenyl group as defined above;
W is hydrogen or hydroxy;
or a stereoisomer thereof or a pharmaceutically acceptable salt thereof.

2. A compound as claimed in claim 1 wherein
R$_1$ is hydrogen; bromo; chloro; a linear C$_1$–C$_3$ alkoxy group or an optionally substituted phenyl group of formula

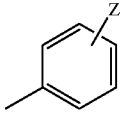

wherein Z is hydrogen, bromo, fluoro, a linear C$_1$–C$_3$ alkoxy group or trifluoromethyl;
R$_2$ is hydrogen, a linear or branched C$_1$–C$_5$ alkyl group or an optionally substituted phenyl group as defined above;
X is CH$_2$, CHOH, or C=NOH;
R$_3$ is hydrogen or a linear or branched C$_1$–C$_5$ alkyl group;
Y is a (CH$_2$)$_n$ group wherein n is zero or 1, C=O or CH-A wherein A is an optionally substituted phenyl group as defined above;
A is an optionally substituted phenyl group as defined above; and
W is hydrogen or hydroxy.

3. A compound selected from the group consisting of:
1) 2-(4-benzyl-piperidin-1-yl)-1-(3-bromo-isoxazol-5 yl)-ethan-1-ol;
2) 2-(4-benzyl-piperidin-1-yl)-1-(3-bromo-isoxazol-5-yl)-propan-1-ol;
3) 2-(4-benzyl-piperidin-1-yl)-1-(3-methoxy-isoxazol-5-yl)-ethan-1-ol;
4) 2-(4-benzyl-piperidin-1-yl)-1-(3-methoxy-isoxazol-5-yl)-propan-1-ol;
5) 2-(4-benzyl-4-hydroxy-piperidin-1-yl)-1-(3-bromo-isoxazol-5-yl)-ethan-1-ol;
6) 2-(4-benzyl-4-hydroxy-piperidin-1-yl)-1-(3-bromo-isoxazol-5-yl)-propan-1-ol;
7) 2-(4-benzyl-4-hydroxy-piperidin-1-yl)-1-(3-methoxy-isoxazol-5-yl)-ethan-1-ol;
8) 2-(4-benzyl-4-hydroxy-piperidin-1-yl)-1-(3-methoxy-isoxazol-5-yl)-propan-1-ol;
9) 2-(4-benzyl-piperidin-1-yl)-1-(3-bromo-isoxazol-5-yl) ethane;
10) 2-(4-benzyl-piperidin-1-yl)-1-(3-methoxy-isoxazol-5-yl)-ethane;
11) 2-(4-benzyl-piperidin-1-yl)-1-(3-bromo-isoxazol-5-yl)-propane;
12) 2-(4-benzyl-piperidin-1-yl)-1-(3-methoxy-isoxazol-5-yl)-propane;
13) 2-(4-benzyl-piperidin-1-yl)-1-(3-bromo-isoxazol-5-yl)-ethan-1-one-oxyme;
14) 2-(4-benzyl-piperidin-1-yl)-1-(3-bromo-isoxazol-5-yl)-propan-1-one-oxyme;
15) 2-(4-benzyl-piperidin-1-yl)-1-(3-methoxy-isoxazol-5-yl)-ethan-1-one-oxyme;
16) 2-(4-benzyl-piperidin-1-yl)-1-(3-methoxy-isoxazol-5-yl)-propan-1-one-oxyme;
17) 2-(4-benzoyl-piperidin-1-yl)-1-(3-bromo-isoxazol-5-yl)-ethan-1-ol;
18) 2-(4-benzoyl-piperidin-1-yl)-1-(3-bromo-isoxazol-5-yl)-propan-1-ol;
19) 2-(4-benzoyl-piperidin-1-yl)-1-(3-methoxy-isoxazol-5-yl)-ethan-1-ol;
20) 2-(4-benzoyl-piperidin-1-yl)-1-(3-methoxy-isoxazol-5-yl)-propan-1-ol;
21) 2-[4-(4-fluoro-benzoyl)piperidin-1-yl]-1-(3-bromoisoxazol-5-yl)-ethan-1-ol;
22) 2-[4-(4-fluoro-benzoyl)piperidin-1-yl]-1-(3-bromoisoxazol-5-yl)-propan-1-ol;
23) 2-[4-(4-fluoro-benzoyl)piperidin-1-yl]-1-(3-methoxyisoxazol-5-yl) ethan-1-ol;
24) 2-[4-(4-fluoro-benzoyl)piperidin-1-yl]-1-(3-methoxyisoxazol-5-yl)propan-1-ol;
25) 2-(4-diphenylmethyl-piperidin-1-yl)-1-(3-bromoisoxazol-5-yl)-propan-1-ol;
26) 2-(4-diphenylmethyl-piperidin-1-yl)-1-(3-bromoisoxazol-5-yl)-ethan-1-ol;
27) 2-(4-diphenylmethyl-piperidin-1-yl)-1-(3-methoxyisoxazol-5-yl)-propan-1-ol;
28) 2-(4-diphenylmethyl-piperidin-1-yl)-1-(3-methoxy-isoxazol-5-yl)-ethan-1-ol;
29) 2-(4-phenyl-4-hydroxy-piperidin-1-yl)-1-(3-bromoisoxazol-5-yl)-ethan-1-ol;
30) 2-(4-phenyl-4-hydroxy-piperidin-1-yl)-1-(3-bromoisoxazol-5-yl)-propan-1-ol;

31) 2-(4-phenyl-4-hydroxy-piperidin-1-yl)-1-(3-methoxyisoxazol-5-yl)-ethan-1-ol;

32) 2-(4-phenyl-4-hydroxy-piperidin-1-yl)-1-(3-methoxyisoxazol-5-yl)-propan-1-ol;

33) 2-(4-phenyl-4-hydroxy-piperidin-1-yl)-1-(3-bromoisoxazol-5-yl)-ethane;

34) 2-(4-phenyl-4-hydroxy-piperidin-1-yl)-1-(3-bromoisoxazol-5-yl)-propane;

and stereoisomers thereof and their pharmaceutically acceptable salts.

4. A process for preparing a compound as defined in claim 1, which process comprises:

(a) reacting a compound of formula (II)

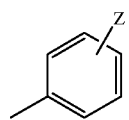

(II)

wherein $R_1$ is hydrogen, bromo; chloro; a linear or branched $C_1$–$C_5$ alkyl group; a linear branched $C_1$–$C_5$ alkoxy group; or an optionally substituted phenyl group of formula

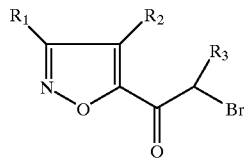

wherein Z is hydrogen, a linear or branched $C_1$–$C_5$ alkyl group, a linear or branched $C_1$–$C_5$ alkoxy group, bromo, chloro, fluoro, nitro or trifluoromethyl;

$R_2$ is hydrogen, a linear or branched $C_1$–$C_5$ alkyl group or an optionally substituted phenyl group as defined above; and $R_3$ is hydrogen or a linear or branched $C_1$–$C_5$ alkyl group;

with a compound of formula (III)

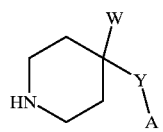

(III)

wherein

Y is a $(CH_2)_n$ group in which n is an integer of 0 to 4, CHOH, C=O, or CH-A wherein A is an optionally substituted phenyl group as defined above;

A is an optionally substituted phenyl group as defined above; and

W is hydrogen or hydroxy;

to obtain a compound of formula (I) wherein $R_1$, $R_2$, $R_3$, Y, A and W are as defined above and X is a C=O group; and, converting a compound of formula (I) as obtained above, into another compound of formula (I) wherein X is CHOH or $CH_2$; or (b) reacting a compound of formula (IV)

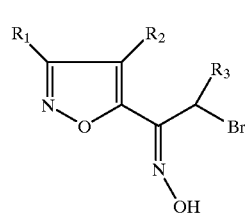

(IV)

wherein $R_1$, $R_2$, and $R_3$ have the meanings above mentioned, with a compound of formula (III) as defined above, to obtain a compound of formula (I) wherein $R_1$, $R_2$, $R_3$, Y, A and W are as defined above and X is a C=NOH group; or (c) reacting a compound formula (V)

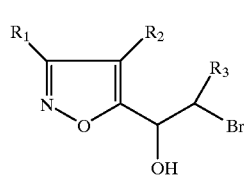

(V)

wherein $R_1$, $R_2$ and $R_3$ have the meanings above mentioned, with a compound of formula (III) as defined above, to obtain a compound of formula (I) wherein $R_1$, $R_2$, $R_3$, Y, A and W are as defined above and X is a CHOH group; or (d) reacting a compound of formula (VI)

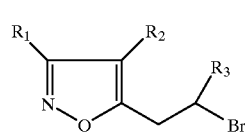

(VI)

wherein $R_1$, $R_2$ and $R_3$ have the meanings above mentioned, with a compound of formula (III) as defined above, to obtain a compound of formula (I) wherein X is $CH_2$; and, if desired, (e) converting a compound of formula (I) into a pharmaceutically acceptable salt thereof.

5. A pharmaceutical composition which comprises, as an active ingredient, an excitatory amino acid receptor inhibitory effective amount of a compound as defined in claim 1 in admixture with a pharmaceutically acceptable carrier and/or diluent.

6. A method of treating neurotoxic action of an excitatory amino acid comprising administering to a patient in need thereof, an excitatory amino acid receptor inhibitory effective amount of at least one compound selected from formula (I) in claim 1.

7. The method of claim 6 neurotoxic action is in acute or degenerative CNS disease.

8. The method of claim 6 said neurotoxic action is in epilepsy, Parkinson's disease, Huntington's disease or Alzheimer's disease.

9. The method of claim 6 said neurotoxic action of an excitatory amino acid (EEA) is at EEA receptors of the central neurons.

* * * * *

CERTIFICATE OF CORRECTION

PATENT NO. : 5,968,955
DATED : October 19, 1999
INVENTOR(S): Sergio MANTEGANI et al.

It is certified that an error appears in the above-identified patent and that said Letters Patent is hereby corrected as shown below:

On the title page, item [30], the Foreign Application Priority Data is incorrect. It should be:

--[30] Foreign Application Priority Data

Oct. 6, 1995  [GB]  United Kingdom...................9520444--

Signed and Sealed this

Nineteenth Day of December, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO. : 5,968,955
DATED : October 19, 1999
INVENTOR(S) : Sergio Mantegani et al.

It is certified that error appears in the above-identified patent and that said Letters Patent is hereby corrected as shown below:

Title page,
Item [86], "PCT/EP95/04075" should read -- PCT/EP96/04075 --.

Column 6,
Line 15, "Hônig's" should read -- Hünig's --;
Line 28, "Hônig's" should read -- Hünig's --;

Signed and Sealed this

Twenty-eighth Day of August, 2001

*Attest:*

NICHOLAS P. GODICI
*Attesting Officer*     *Acting Director of the United States Patent and Trademark Office*